United States Patent [19]

Drumm

[11] Patent Number: 4,969,816
[45] Date of Patent: Nov. 13, 1990

[54] DENTAL MATERIAL CARRIER AND APPLICATOR

[76] Inventor: Melvin Drumm, 585 Avon Dr., Orange, Conn. 06477

[21] Appl. No.: 325,367

[22] Filed: Mar. 20, 1989

[51] Int. Cl.⁵ .............................................. A61C 5/04
[52] U.S. Cl. .................................................... 433/90
[58] Field of Search ...................... 433/89, 90; 222/575

[56] References Cited

U.S. PATENT DOCUMENTS

| | | | |
|---|---|---|---|
| 1,015,039 | 1/1912 | Lasbury | 433/89 X |
| 1,712,139 | 5/1929 | Espinola | 433/90 |
| 4,391,590 | 7/1983 | Dougherty | 433/90 |
| 4,767,326 | 8/1988 | Bennett et al. | 433/90 |
| 4,798,596 | 1/1989 | Mühlbauer | 433/90 X |

Primary Examiner—Gene Mancene
Assistant Examiner—R. Thomas Price
Attorney, Agent, or Firm—Arthur T. Fattibene

[57] ABSTRACT

This disclosure is directed to a dental material carrier and applicator in the form of a syringe capsule for containing a supply of dental material, e.g. a dental lining material for treating exposed dental pulp that has formed on the end thereof adjacent the discharging nozzle or orifice an applicator configuration for facilitating the positioning of the material as the dentist is applying the material contained within the capsule.

1 Claim, 1 Drawing Sheet

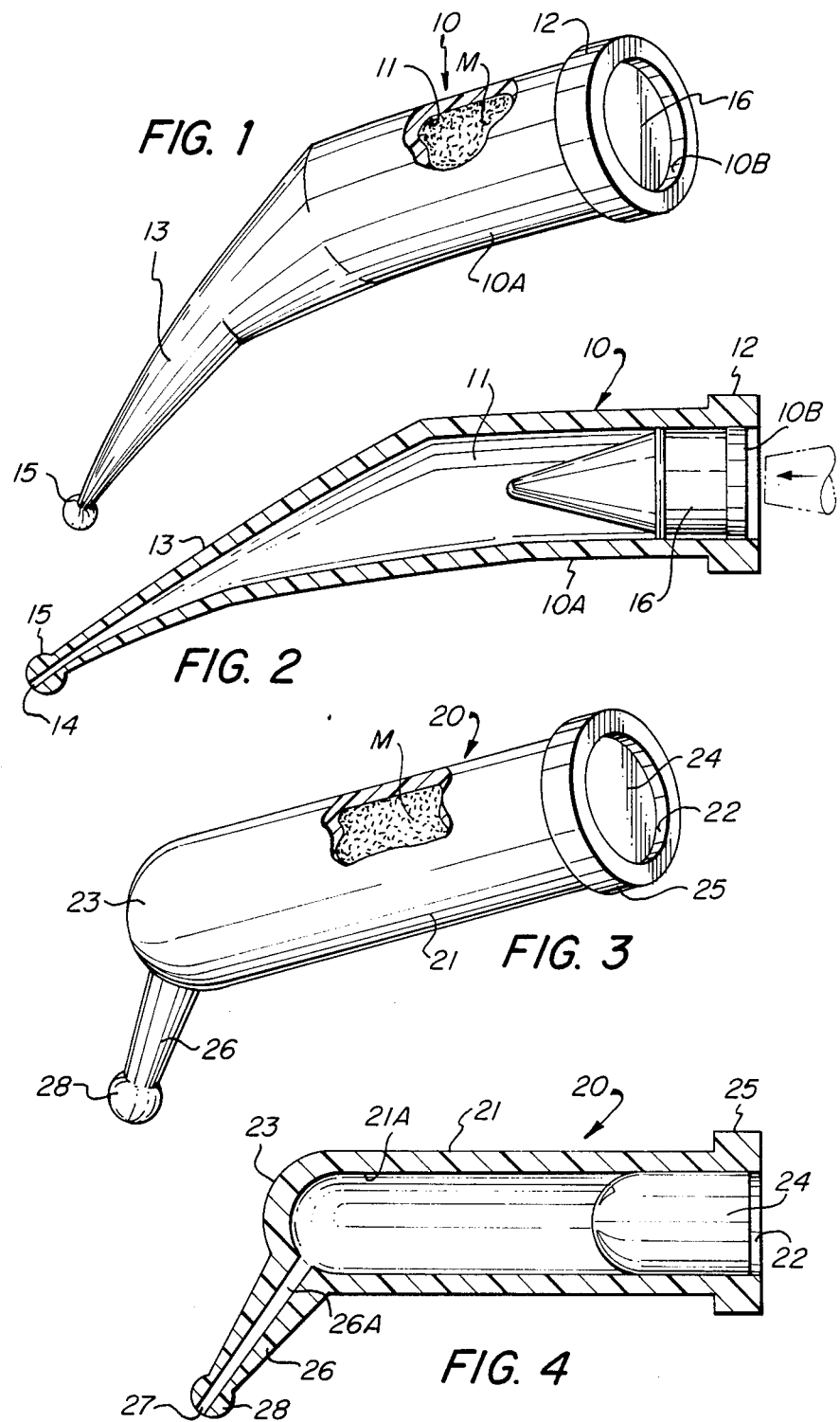

DENTAL MATERIAL CARRIER AND APPLICATOR

1. Field of Invention

This invention is directed to the field of dentistry, and more specifically to an improved capsule construction or syringe tip adapted to contain a predetermined amount of a dental material and having an applicator formed on the end thereof through which the material is dispensed as it is applied to the treated part.

2. Problem and Prior Art

Dental syringes and disposable capsules for use therewith have been known for some years. U.S. Pat. No. 3,581,399 issued to William B. Dragan is one such known dental syringe. Numerous other patents have been granted for other variations of disposable dental capsules and/or dental syringe holders for use therewith. U.S. Pat. Nos. 3,900,954 and 4,198,756 are examples of such other known constructions Other patents have been granted for essentially similar type syringe holders and capsules for use therewith such as U.S. Pat. Nos. 4,295,828; 4,330,280; 4,384,853 and 4,391,590. Capsules for such use with the dental syringes disclosed in the foregoing patents have also been developed for use in performing certain specific dental procedures, e.g. the placing of a composite resin in a tooth, or bonding and/or for use in cosmetic dentistry as disclosed in certain of the prior issued or known patents, e.g. U.S. Pat. Nos. 4,682,950; DES 289,682; DES 292,825 and U.S. Pat. No. 4,768,954. A needle tube or capsule as disclosed in a co-pending application Ser. No. 261,600 filed on or about Oct. 24, 1988, discloses another disposable capsule for a specific dental procedure, e.g. for setting posts.

In a number of specific dental procedures, it is imperative that certain material be applied with an applicating device permitting the dentist to dab the dental material onto the tooth, tissues or tooth pulp being treated For example, when applying an astringent or hemostatic material to stop bleeding, a dentist would use an applicator to pick up minute portions of the astringent material which he would then dab onto the tissue or part being treated. This required a time consuming operation since the dentist had to repeatedly move the applicator from the material supply to the tooth or part being treated. A similar procedure is encountered in treating exposed dental pulp. It has been recently discovered, i.e. in the 1940's and 1950's, that dental pulp, like other body parts, could be healed if subjected to proper treatment. The discovery of calcium hydroxide as a means for healing dental pulp has gained accpetance in the profession as a treatment for injured dental pulp. Accordingly, various brand name compounds containing calcium hydroxide have gained prominence for treating dental pulp. However, the recommended procedure for applying such brand name calcium hydroxide compounds consisted of utilizing an applicating instrument having a tip end which was required to be repeatedly dipped into a supply of such calcium hydroxide compound, which then had to be carried on the end of such applicator to the sight of the treated part wherein the compound on the tip of the applicator was then transferred to the injured or treated part by dabbing the end of the instrument onto the injured part. This procedure was a painstaking and time consuming operation since the dentist had to repeatedly transfer minute portions of the treating material from the material source to the injured part numerous times. This was because the applicator tool could only accommodate minute amounts of the treating material. With the advent of light activated calcium hydroxide materials, e.g. Prisma VLC Dycal, the problem of application of such material was somewhat aggravated for the reason that the working time was limited by the curing effect which visible light had on the material. The application of pit and sealant materials was also frequently performed by a similar procedure. The various known capsule constructions as evidenced by those disclosed in the hereinbefore mentioned patents were not suitable in the foregoing described procedures, as they lacked an applicator for dabbing the material onto the injured part

OBJECTS

An object of this invention is to provide an improve capsule construction capable of holding a predetermined amount of a dental material which includes an applicator whereby the material supply carried therein can be dabbed or minutely applied to an injured part as may be required.

Another object of this invention is to provide a carrier and applicator device for dabbing dental materials upon an injured part in a convenient and expedient manner.

Another object of the invention is to provide a combined material supply carrier and applicator which will eliminate the heretofore recommended procedure of repeatedly transporting minute quantities of a dental material from a supply source to the sight of the treatment.

Another object of this invention resides in an improved applicating capsule which is readily simple in construction and which can be readily fabricated.

Another object is to provide an applicating capsule or syringe tip which can be readily utilized with the known syringe constructions.

SUMMARY OF THE INVENTION

The foregoing objects and other features and advantages are obtained by an improved dental syringe tip or capsule that includes a body portion defining a reservoir for containing a predetermined amount of a dental treating material, e.g. an astringent or hemostatic material, calcium hydroxide compound or other treatment material, that is required to be dabbed onto the injured or treated part. The capsule also includes a discharge nozzle terminating in a discharge orifice disposed in communication with the reservoir. Integrally formed on the external surface of the discharge nozzle and about the discharge orifice is an enlarged protuberance or ball shaped applicator whereby the material exiting the discharge orifice can be dabbed upon the part being treated. The applicator on the end of the tip can also be used as a burnishing tool to flow the material where desired. A displaceable piston seals the end of the reservoir and provides the means for effecting the extrusion of the material from the capsule as needed as the piston is displaced upon the actuation of a plunger of an associated syringe or holder for the capsule.

FEATURES

A feature of this invention resides in an improved syringe tip construction which includes a ball applicator formed on the discharge end of the nozzle to facilitate the placement of a dental material upon an injured or treated part.

Another feature resides in a capsule or syringe tip capable of containing a predeterminate amount of material having an applicator for on the discharge end thereof for burnishing or placing small quantities of material onto the treated part.

Other features and advantages will become more readily apparent when considered in view of the drawings in which:

FIG. 1 illustrates a perspective view of a capsule or syringe tip embodying the present invention.

FIG. 2 is a sectional side view of the tip construction of FIG. 1.

FIG. 3 is a perspective view of a modified tip construction embodying the invention.

FIG. 4 is a sectional side view of the tip of FIG. 3.

DETAIL DESCRIPTION

Referring to the drawings, there is shwon in FIGS. 1 and 2 one embodiment of the present invention. As shown, the syringe tip or capsule 10 comprises a generally cylindrical body portion 10A defining a reservoir for containing a predetermined type of dental material, e.g. an astringent or hemostatic material, a calcium hydroxide type compound, a sealant or any other material M that is required to be dabbed onto an injured or treated part, e.g. tissue or dental pulp or the like. One end of the body portion 10A is provided with a full open end 10B which is suitably sealed by a displaceable piston 12 to seal the material M within the syringe tip 10. Circumscribing the full open end 10B of the body portion 10A is a laterally extending flange or collar 12.

Connected to the other end of the body portion 10A and in communication with the reservoir is a discharging nozzle 13. As shown in FIG. 1, the internal surface of the nozzle 13 tapers inwardly toward a discharge orifice 14. It will be understood that the opening defined by the discharge orifice 14 may range from approximately 0.5 mm to 1. mm or larger, depending upon the flow characteristic of the treating material M. In accordance with this invention, the external surface of the nozzle 13 adjacent the tip or discharge orifice 14 is provided with an enlarged protuberance, which in the illustrated embodiment comprises a ball shaped applicator 15 that circumscribes the orifice 14 In the illustrated embodiment, it will be noted that the treating material M within the capsule 10 can be dispensed as required by the displacement of the piston 16, and the ball applicator 15 formed on the tip end of the capsule enables the dentist to utilize the capsule 10 as a burnishing tool to spread or dab the treating material onto the injured part as required. It will be understood that the reservoir is sufficiently large so as to hold the required amount of material to complete a given procedure and from which the material can be dispensed in the minute quantities necessary for the procedures herein described. Because the treating material M is readily available at the discharge end of the capsule 10, the repetitive motion of transferring the treating material from a supply source, which heretofore comprised a dental pad upon which the material was placed, to the injury or treated part, is completely eliminated.

If desired, the material from which the capsule 10 is formed may be made of a light opaque material, in the event the capsule 10 is to be used with light activated materials. It will also be noted that the capsule 10 may also be preloaded with the suitable dental material M as herein described, in which case the capsule 10 comprises the shipping package for the material M, the dispensing means for the material and the applicator for spreading or dabbing the material on the injured part. When utilized as a package for the material M, a removable sealing cap (not shown) may be fitted over the orifice 14 to seal the capsule at the orifice end.

The capsule 10 described is also suitable for use with a composite resin filling material. The applicator or ball end 15 will enable a dentist to pack or tamper the compsite resin as it is injected into a tooth cavity to ensure that the composite material is compacted into the sight of the restoration to insure a dense, void-free restoration.

As shown in FIGS. 1 and 2, the discharge nozzle is angled relative to the longitudinal axis of the body portion 10A. The size of the capsule 10 is such that it can be utilized with any of the patented dental syringes disclosed in the foregoing mentioned patents.

FIGS. 3 and 4 illustrate a modified form of the invention. As shown, the configuration of the capsule 20 comprises a cylindrical body portion 21 that is open at one end 22 and is provided with a curvilinear end wall 23 at the other end thereof. The open end 22 is sealed by a displaceable piston 24; and a laterally outwardly extending flange or collar 25 circumscribes the open end 22, as hereinbefore described. The internal bore 21A of the body portion 21 thus defines a reservoir for containing the dental material M.

A discharge nozzle 26 is connected to the curvilinear end 23 of the capsule 20. As best seen in FIG. 4, the nozzle is provided with a capillary bore or passageway 26A which is in communication with the reservoir 21A defined by the body portion 21 at one end, and which other end terminates in a discharge orifice 27. As hereinbefore described, the end of the nozzle 26 at the orifice 27 thereof is provided with a protuberance or ball applicator 28 which circumscribes the orifice opening 27. The passageway 26A is a general uniform intern diameter throughout forming a capillary bore 26A extending the length of the nozzle, which is disposed at an angle relative to the longitudinal axis of the capsule 20. In all other respects, the capsule of FIGS. 3 and 4 is similar to that described with respect to FIGS. 1 and 2.

From the foregoing, it will be apparent that the described capsule having a ball applicator at the tip or orifice end thereof, provides the dentist with a tool that permits the treating material to be dispensed as needed and at the same time gives the dentist an applicating tool to "work" the material onto the injured part without the need of going through the tedium and repetitious motion of picking the material up from a dentist pad and transporting the material on the end of an applicating tool for deposit at the sight of the injury.

While the invention has been described with respect to several embodiments, it will be understood and appreciated by one skilled in the art that variations and modifications may be made without departing from the spirit or scope of the invention.

What is claimed is:

1. An integrally formed disposable plastic capsule for containing and applying a dental material to a treatment area comprising a body portion defining a reservoir for containing a predetermined amount of dental material, said body portion having a full open end, a lateral outwardly extending flange circumscribing said open end, a displaceable piston contained within said body portion for sealing said full open end, a discharge nozzle connected to the other end of said body portion, said discharge nozzle having a passageway extending therethrough and terminating in a discharge orifice, said discharge nozzle being disposed at an angle relative to the longitudinal axis of said body portion, and a protuberance integrally formed at the end of said discharge nozzle, said protuberance defining a small ball applicator formed about said discharge orifice whereby the dental material contained within the capsule can be readily dispensed by displacement of said piston permitting the dentist to work the material onto the injured part by said ball applicator.

* * * * *